United States Patent [19]

Brand et al.

[11] Patent Number: 4,754,052

[45] Date of Patent: Jun. 28, 1988

[54] METHOD FOR RECOVERING DIPHENYLETHERS FROM THEIR NITRATED BY-PRODUCTS

[75] Inventors: William W. Brand, Chadds Ford; John F. Stephen, West Chester, both of Pa.

[73] Assignee: ICI Americas Inc., Wilmington, Del.

[21] Appl. No.: 928,901

[22] Filed: Nov. 7, 1986

[51] Int. Cl.[4] .............................................. C07C 79/46
[52] U.S. Cl. ...................................... 560/21; 562/435; 564/87; 564/166; 564/171; 558/257; 558/416
[58] Field of Search .......................... 560/21; 562/435; 564/87, 160, 171; 558/416, 257

[56] References Cited

U.S. PATENT DOCUMENTS

| | | | |
|---|---|---|---|
| 3,862,209 | 1/1975 | Theissen | 71/103 |
| 3,928,416 | 12/1975 | Bayer et al. | 71/103 |
| 4,004,530 | 1/1987 | Grove, deceased | 71/103 |
| 4,031,131 | 6/1977 | Johnson | 71/103 |
| 4,262,152 | 4/1981 | Johnson | 71/103 |
| 4,285,723 | 8/1981 | Cartwright et al. | 71/103 |
| 4,311,515 | 1/1982 | Grove | 71/103 |
| 4,313,000 | 1/1982 | Kruse et al. | 71/103 |
| 4,314,078 | 2/1982 | Kruse et al. | 71/103 |
| 4,369,316 | 1/1983 | Kruse et al. | 71/103 |
| 4,424,393 | 1/1984 | Guzik et al. | 71/103 |
| 4,589,914 | 5/1986 | Cartwright | 71/103 |
| 4,596,883 | 6/1986 | Schwindeman et al. | 71/103 |

OTHER PUBLICATIONS

Sidgwick, N. V., "The Organic Chemistry of Nitrogen", 3rd Rev. Ed., 1966, pp. 140–142 and 387–391.
Chung, S. K., *J. Org. Chem.*, 46, 1981, pp. 5457–5458.
Mahood, S. A. and Schaffner, P. V. L., Org. Syn., C.V. 2, 1955, pp. 160–163.
Smith, L. I. and Opic, J. W., Org. Syn., C.V. 3, 1955, 56–58.
DeLaMare, P. B. D. and Ridd, J. H., "Aromatic Substitution: Nitration and Halogenation", 1959, pp. 48–53.
Rylander, P. N., "Catalytic Hydrogenation over Platinum Metals", *Academic Press*, 1967, pp. 168–202.
Kamm, O., Org. Synth. C.V.I., vol. I, 2nd Ed., 1941, pp. 445–447.
Doyle, M. P. et al, "Reductive Deamination of Arylamines by Alkyl Nitrites in N,N-Dimethylformamide, A Direct Conversion of Arylamines to Aromatic Hydrocarbons", *Journal of Organic Chemistry*, vol. 42, No. 22, 1977, pp. 3494–3498.
Kornblum, N., Organic Reactions, vol. 2, 1944, pp. 262–340.
Zollinger, Heinrich, "Homolytic Reactions of Diazo Compounds", *Azo and Diazo Chemistry, Aliphatic and Aromatic Compounds*, pp. 153–159 (1961).
Nickson, T. E., "A Unique Application of the Sulfide Reduction Useful for the Preparation of Isomerically Pure Aromatic Nitro Compounds and Anilines", *J. Org. Chem.*, 51, 3903 (1986).

*Primary Examiner*—Paul J. Killos
*Attorney, Agent, or Firm*—John Wilson Jones

[57] ABSTRACT

A process of recycling nitrated by-products formed during the manufacture of the compound of the formula

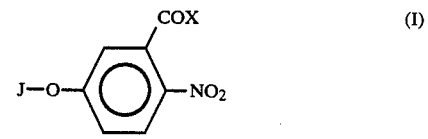

and salts thereof
wherein J is

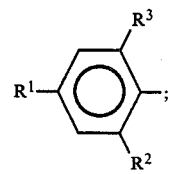

and further wherein:
$R^1$ is fluorine, chlorine, bromine, or iodine or a trifluoromethyl group;
$R^2$ is a hydrogen atom, a fluorine, chlorine, bromine or iodine atom or a trifluoromethyl group;
$R^3$ is a hydrogen atom, a $C_1$–$C_4$ alkyl group, a trifluoromethyl group, a cyano group or a fluorine, chlorine, bromine or iodine group; X is

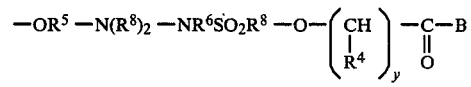

$R^4$ is $R^5$ or an acyl radical of the formula

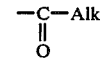

wherein Alk is a $C_{1-6}$ alkyl group;
$R^5$ is a hydrogen atom or a $C_{1-6}$ alkyl group optionally substituted with either one or more halogen atoms or a phenyl group;
B is a $C_{1-10}$ alkyl, $OR^7$ or $SR^7$;
y is 1 to 4;
$R^6$ is a hydrogen atom or a $C_{1-2}$ alkyl group;
$R^7$ is hydrogen, or a $C_{1-8}$ alkyl group, a $C_{3-8}$ cycloalkyl group, an agronomically acceptable cationic salt, or a

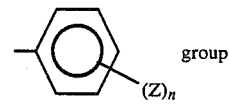

wherein n is 0 to 3 and Z is selected from the group consisting of halogen, a $C_{1-10}$ alkyl or alkoxy group, cyano, nitro, and trifluoromethyl; and
$R^8$ is $R^5$ or a $C_{1-6}$ alkoxy group. The process comprises 2 stages. In the first stage, the nitrated by-products are reduced. In the second stage, the reduced compounds are diazotized and the diazonium group is replaced with a hydrogen atom.

18 Claims, No Drawings

METHOD FOR RECOVERING DIPHENYLETHERS FROM THEIR NITRATED BY-PRODUCTS

BACKGROUND OF THE INVENTION

1. Field of the Invention

This invention relates to an improved process for increasing efficiency in the production of nitrated diphenylethers. In particular, it is directed to a process for recovering diphenylether reactants from their nitrated by-products.

2. Description of the Prior Art

The prior art discloses a wide range of diphenylether compounds useful as herbicides. Such diphenylethers are of the structural formula

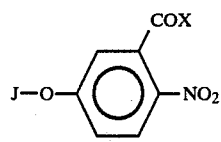 (I)

and salts thereof, wherein J is

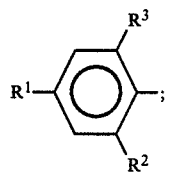

$R^1$ is a fluorine, chlorine, bromine, or iodine atom or a trifluoromethyl group;

$R^2$ is a hydrogen, fluorine, chlorine, bromine or iodine atom or a trifluoromethyl group;

$R^3$ is a hydrogen, fluorine, chlorine, bromine or iodine atom, or a $C_1$-$C_4$ alkyl, trifluoromethyl, or cyano group;

X is

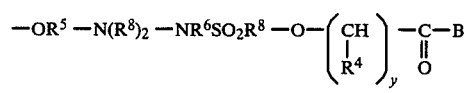

$R^4$ is $R^5$ or an acyl radical of the formula

wherein Alk is a $C_{1-6}$ alkyl group;

$R^5$ is a hydrogen atom or a $C_{1-6}$ alkyl group optionally substituted with either one or more halogen atoms or a phenyl group;

B is a $C_{1-10}$ alkyl, $OR^7$ or $SR^7$;

y is 1 to 4;

$R^6$ is a hydrogen atom or a $C_{1-2}$ alkyl group;

$R^7$ is hydrogen, or a $C_{1-8}$ alkyl or $C_{3-8}$ cycloalkyl group, an agronomically acceptable cationic salt, or a

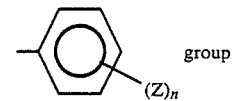

wherein n is 0 t 3

Z is selected from the group consisting of a halogen atom or a $C_{1-10}$ alkyl or $C_{1-10}$ alkoxy group, cyano, nitro, and trifluoromethyl group; and $R^8$ is $R^5$ or a $C_{1-6}$ alkoxy group. Particularly effective as herbicides are those compounds disclosed in U.S. Pat. Nos. 4,031,131, 4,285,723, 4,424,393 and 4,400,530 wherein A.
$R^1$ is a chlorine atom or a trifluoromethyl group;
$R^2$ is a hydrogen or fluorine atom
$R^3$ is a chlorine atom; and
X is —$OR^4$ or $NR^6SO_2R^8$ wherein
$R^4$ is a hydrogen atom;
$R^6$ is a hydrogen atom; and
$R^8$ is methyl or ethyl.

Especially preferred are the compounds wherein
(i) X is —$OR^4$; $R^1$ is —$CF_3$; $R^2$ is —H; $R^3$ is—Cl; and $R^4$ is hydrogen;
(ii) X is —$OR^4$; $R^1$ is —$CF_3$; $R^2$ is —F; $R^3$ is—Cl; and $R^4$ is hydrogen;
(iii) X is —$NR^6SO_2R^8$; $R^1$ is —$CF_3$; $R^2$ is —H or —F; $R^3$ is —Cl; $R^6$ is —H and $R^8$ is —$CH_3$,
(iv) X is —$NR^6SO_2R^8$; $R^1$ is —$CF_3$; $R^2$ is —H or —F; $R^3$ is —Cl; $R^6$ is —H; and $R^8$ is —$C_2H_5$.

B.
$R^1$ is a halogen atom or a trifluoromethyl group;
$R^2$ is hydrogen or halogen;
$R^3$ is hydrogen, halogen, cyano, trifluoromethyl, or a $C_{1-4}$ alkyl group X is

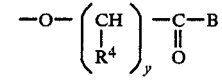

y is 1;
$R^4$ is selected from the group consisting of hydrogen, $C_{1-4}$ alkyl, and hydroxy alkyl ($C_{1-4}$);
B is $SR^7$ or —$OR^7$;
$R^7$ is hydrogen, or a $C_{1-8}$ alkyl group, a $C_{3-8}$ cycloalkyl group or an agronomically acceptable cationic salt, or a

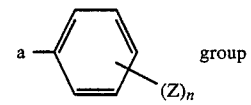

wherein n is 0 to 3 and Z is selected from the group consisting of halogen, a $C_{1-10}$ alkyl or alkoxy group, cyano, nitro, and trifluoromethyl.

Particularly effective are those compounds wherein

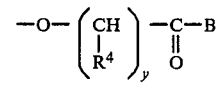

y is 1;
B is —$OR^7$, $R^7$ is —$C_2H_5$, $R^4$ is either —H or —$CH_3$;

$R^1$ is trifluoromethyl;
$R^3$ is chlorine; and
$R^2$ is H.

The compounds represented by formula (I) are produced by the following reaction sequence;

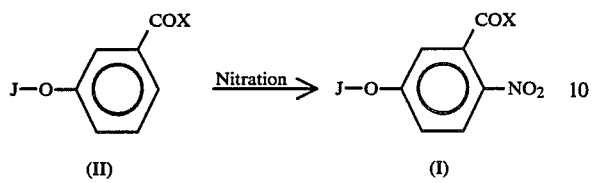

wherein J and X are the substituents recited above.

Any nitration technique conventional in the art may be employed. Exemplary of nitration conditions are those disclosed in U.S. Pat. Nos. 4,285,723; 4,031,131; and 4,400,530. In general this nitration reaction is carried out at a temperature of about 0° to about 70° C. in the presence of an electrophilic nitrating agent. While any conventional nitrating agent may be used, preferred are nitric acid/sulfuric acid, potassium nitrate/sulfuric acid or nitric acid/sulfuric acid/acetic anhydride. An inert organic solvent, i.e., a solvent inert to the reactants as well as the nitrated products, can also be used. Exemplary of inert organic solvents are $C_5$-$C_{12}$ aliphatic hydrocarbons; $C_5$-$C_7$ cyclic aliphatic hydrocarbons; and $C_1$-$C_6$ halogenated aliphatic hydrocarbons. Some examples of suitable solvents are diethyl ether, cyclohexane, hexane, heptane, methylene chloride, ethylene dichloride, chloroform, and perchloroethylene. A chlorinated hydrocarbon is particularly preferred and especially methylene dichloride, ethylene dichloride, chloroform and perchloroethylene. Most preferably, the nitration proceeds in concentrated nitric acid (90-100%) with a mole ratio of nitric acid to reactant (II) between about 5-20 to 1.

Generally, 50-80% by weight of the final product is of structural formula (I) and 20-50% by weight are the nitrated by-products, represented by the structural formula

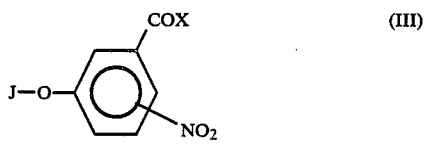

A method of recovering the product represented by the formula (II) is therefore desired.

SUMMARY OF THE INVENTION

It is an object of this invention to develop a process for increasing the yield of the desired nitrated compound of the structural formula (I) by recycling the nitrated by-products of formula (III) to obtain the product (II). As a result of this process, most of the 20-50 weight percent of the nitrated by-products may be recovered and recycled. The overall efficiency of the nitration process is dramatically improved by the recycling procedure of this invention.

The process of this invention involves essentially two stages. In the first stage, the nitro group of the undesired isomers of structural formula (III) are reduced to amino groups. In the second stage, the amino groups are diazotized and the resulting diazonium groups are replaced by hydrogen to render the nitration precursor, (II).

While effectively increasing the useful yield of the desired nitrated product, the amount of undesired waste products is further decreased. Compound (II) may then be re-nitrated. Theses stages may be repeated until optimum recovery of the desired nitrated compound is btained. The reaction sequence of this invention may be summarized as follows;

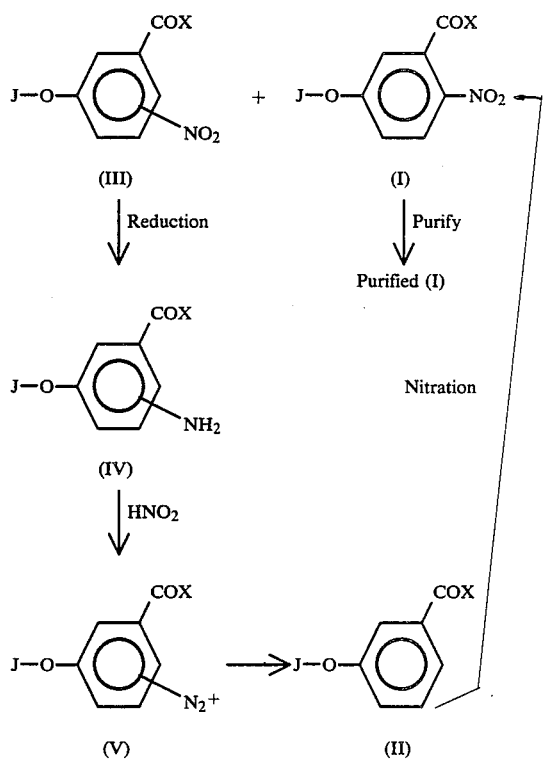

DETAILED DESCRIPTION OF THE INVENTION

The process of this invention comprises two crucial steps. These steps are:
1. reduction of the nitro to amino groups;
2. diazotization of the resulting amino groups and replacement of the diazonium group by hydrogen to regenerate the starting compound (II) for the nitration reaction.

The desired nitro compound obtained is first separated from the nitrated by-products. This may be achieved by any conventional separation technique, such as those disclosed in U.S. Pat. Nos. 4,031,131; 4,285,723; 4,400,530; 4,424,393. Separation by recrystallization, liquid chromatography or distillation are especially preferred.

I. Reduction of the Nitro Group

The reduction of the nitrated by-products may be conducted on the recrystallization filtrate or distillate directly. When separation is by recrystallization, it is often desired to replace the recrystallization solvent with a second solvent since chioce of solvents in hydrogenation reactions often affects the overall efficiency of the reaction. For example where reduction occurs in the presence of dithionite, a water-miscible solvent, such as an alkanol, preferably those with 1-3 carbon atoms, such as ethanol, is preferred. The replacement of the recrystallization solvent with a second solvent is normally achieved by stripping. Most preferably the second solvent is ethanol since this alkanol does not inhibit catalytic hydrogenation, and further, may serve as the deamination reagent in the second stage.

Preferably, reduction proceeds by catalytic hydrogenation, dithionite reduction or by metal/acid reduction. Of these three, catalytic hydrogenation and metal/acid reduction are the most preferred.

The catalyst employed in the hydrogenation reaction is preferably either Pt or Pd. The amount of the catalyst normally employed in the reaction is between 0.1 and 10.0, preferably between 0.1 and 1.0, percent by weight of the nitrated by-product produced. At least three equivalents of hydrogen per one equivalent of nitro group to be reduced are generally used. The reduced product is isolated and after the catalyst is filtered off and the solvent evaporated, yields greater than 90% are obtained. Such reactions are performed at pressures of approximately 1 to 4 atmospheres. Most preferably pressures equal to or slightly above 1 atmosphere are employed. The reaction is generally conducted at a temperature between 0° and 50° C., preferably between 20° and 30° C., and most preferably at ambient temperature.

When the "X" substituent of formula (II) is other than —OH, the amount of hydrolysis increases with an increase in pH of the reaction medium. Preferably, therefore, prior to performing the reduction, the pH of the reaction mixture is adjusted to a pH value less than 3, and most preferably less than 1, by adding to the mixture a strong acid. When X is —OH, the pH of the mixture is preferably between 8 and 9.0.

The reduction may also proceed by reducing the nitro groups with an inorganic reducing agent such as sodium dithionite, $Na_2S_2O_4$. Preferably, 3 reducing equivalents are required per mol of nitro group reduced. At the beginning of the reaction, an aqueous basic reaction medium is employed. Preferably the pH is greater than 8.0 and most preferably is between 10 and 12. Atmospheric pressure is normally used. Cooling is further employed to keep the reaction medium below 30° C. The reaction mixture is then stirred at ambient temperature.

A third method of reducing the nitro groups is by a metal/acid reduction process. This process requires a strong inorganic acid, such as hydrochloric, sulfuric, phosphoric and nitric acid and a member selected from the group consisting of Fe, Zn, Sn, $SnCl_2$, $SnCl_4$, $TiCl_3$, $Ti_3(SO_4)_2$ and Al. At least three equivalents of this metal and six equivalents of acid per equivalent of nitro group of formula (III) to be reduced is required. The reaction medium is preferably either water or a $C_{1-4}$ alkanol/water mixture.

The reaction proceeds at an elevated temperature, preferably at reflux, until completion.

II. Diazotization of Anilines and Deamination.

In the second stage of the reaction scheme, the amino groups are diazotized and the diazonium group is replaced with a hydrogen atom.

In general this process can be achieved by first dissolving or suspending the amine in a cold aqueous mineral acid, such as HCl, $H_2SO_4$, $H_3PO_4$, and $HNO_3$. Sodium nitrite and a reducing reagent which promotes deamination either during or subsequent to diazotization is then added to the reaction vessel. This reagent is selected from the group consisting of primary alkanols of 1 to 6 carbon atoms, an alkanol-ether of the formula $R^9$—O—$R^{10}$—OH wherein $R^9$ and $R^{10}$ are $C_1$-$C_6$ alkyl and $C_{1-6}$ alkylene groups, respectively, hypophosphorous acid, $CH_2O/OH^-$, a heavy metal such as zinc or copper, sodium stannite, hydroquinone, ferrous hydroxide, glucose, copper hydride, sodium hydrosulfite and mixtures thereof. Most preferred is $H_3PO_2$ or ethanol. At least one equivalent of the reducing agent promoting deamination and at least one equivalent of sodium nitrite are employed per equivalent of amine. Where ethanol is employed as the solvent for reduction, it normally is unnecessary to add any additional ethanol to the reaction vessel in this step.

Generally, the reaction is allowed to proceed at 0° to 15° C. for 15 to 45 minutes, and generally not more than 30 minutes. The reaction mixture is subsequently heated between 25° and 120° C. for 15 minutes to 3 hours. Most preferably the reaction proceeds at reflux, and does not exceed 120° C.

Where the compound represented by formula (IV) wherein X is either:
- —$N(R^8)_2$ wherein at least one $R^8$ is hydrogen; or
- —$NR^6SO_2R^8$ wherein $R^6$ is hydrogen is diazotized, a nitrogen-containing heterocyclic ring by-product, represented by the formula (VI)

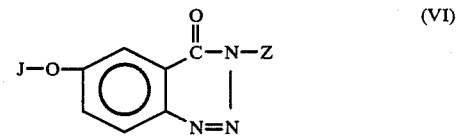

wherein Z is $R^5$ or $SO_2R^8$ and $R^5$, J, and $R^8$ are herein defined, is readily formed. Further, when deamination proceeds in the presence of ethanol, the by-product (VII) represented as

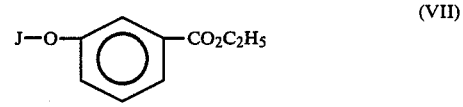

readily forms. Preferably, a catalytic amount of $CuSO_4$ is added to the reaction mixture in order to prevent the build-up of the compounds represented by formulae (VI) and (VII). Preferably, 0.1–10 mol percent of $CuSO_4$ is added to the reaction mixture. Deamination reaction times may be up to six fold longer when $CuSO_4$ is not employed.

The reclaimed product of structural formula (II) is usually isolated prior to reintroduction to the nitrating agent. Such isolation is generally a purification process comprising either recrystallization or distillation steps.

The examples which follow are presented to illustrate the invention and the advantages thereof.

They are not, however, intended to limit the scope of the invention.

EXAMPLE 1

This example illustrates the reduction and deamination of a crude nitration by-product mixture according to the reaction:

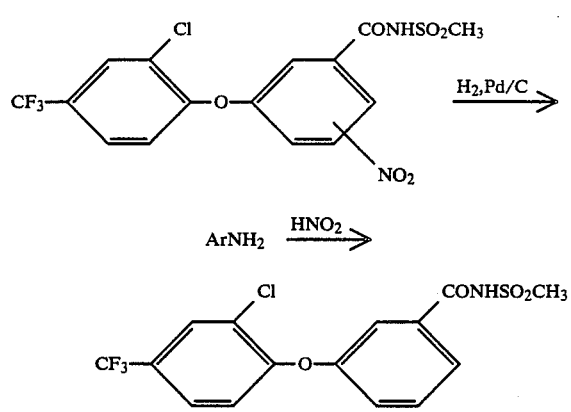

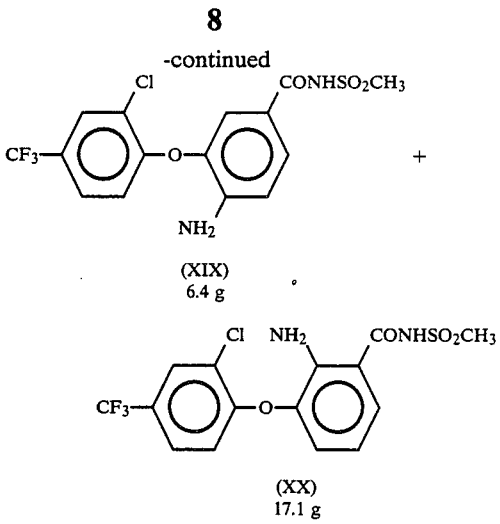

A crude nitration recrystallization filtrate (XIV) containing 11.3 g of (XV), 6.6 g of (XVI), and 19.2 g of (XVII) wherein XV, XVI and XVII are represented by (0.0719 mole total) (total yield of reduction product=85%).

To the resulting ethanol filtrate was added 0.70 g (0.0028 mole) of CuSO$_4$.5H$_2$O, followed by the dropwise addition of 58.4 ml (0.70 mole) of concentrated HCl. To the solution was added dropwise 25.7 g (0.37 mole) of NaNO$_2$ in 57 ml of H$_2$O over 50 minutes. A cooling bath was used intermittently to keep the temperature between 20° and 25° C. The mixture was then stirred at ambient temperature for 30 minutes, followed by slow warming to control foaming due to nitrogen evolution. The mixture was heated at reflux for 1.5 hours. The reaction mixture was then cooled and concentrated. The residue was partitioned between 200 ml of methyl ethyl ketone (MEK) and 100 ml of H$_2$O. The MEK solution was dried and concentrated, leaving 65.2 g of a dark semi-solid which was shown by HPLC to contain 22.4 g of (XIII). Recrystallization from 67 g of toluene gave a 20.3 g of a tan solid which HPLC showed to be 83% pure (XIII) giving an overall yield 50% based on the total ArNO$_2$ (XV+XVI+XVII) in the recrystallization filtrate.

respectively, was produced according to procedures well known in the art. (See in particular Example 2 of U. S. Pat. No. 4,285,723.)

The filtrate was concentrated to dryness, and the recrystallization solvent was replaced with 400 ml of ethanol, and the resulting solution passed through a column packed with 40 g of Darco G60. The pH of the solution was adjusted to 0.36 with concentrated H$_2$SO$_4$, and then 6.0 g of 5% Pd/C was added. The mixture was then hydrogenated in a Paar apparatus for 1.75 hr while maintaining the hydrogen pressure at 50 lbs. The catalyst was then removed by filtration. HPLC of the resulting ethanol filtrate showed it to contain

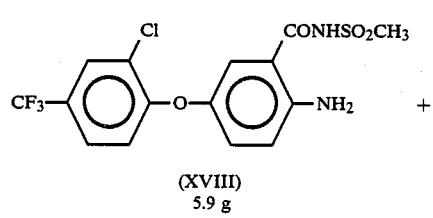

EXAMPLE 2

This example illustrates the hydrogenation of 5-(2-chloro-4-trifluoromethylphenoxy)-N-methanesulfonyl-2-nitrobenzamide, as represented by the following:

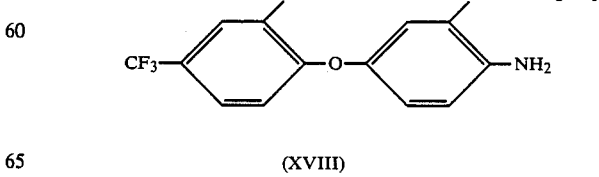

A mixture of 21.96 g (0.05 mol) of (XV), 100 ml of ethanol, and 1.0 g of 5% Pd on carbon (Englehard) was placed in a Paar Hydrogenator and pressurized to 60 psi with hydrogen. The mixture was shaken, and the hydrogen was periodically replenished during 1 hour, after which hydrogen uptake ceased. After the theoretical amount of hydrogen had been absorbed, the reaction mixture was filtered, and the catalyst was washed with ethyl acetate to dissolve the precipitated product. The yellow filtrate was then concentrated at reduced pressure leaving 18.88 g of product (XVIII) as a yellow solid (92% of theoretical), melting point: 183°–186° C. TLC and infra red showed complete reduction of the nitro group to amine.

EXAMPLE 3-5

The reduction of Example 2 was repeated, but using less catalyst and different solvents. The following results were obtained:

| Example No. | Solvent | Amt. Pd/C | Time for Complete H$_2$ Uptake |
| --- | --- | --- | --- |
| 3 | EtOH | 0.22 g | 6 hr. |
| 4 | BuOH | 0.22 g | 12.5 hr. |
| 5 | BuOCH$_2$CH$_2$OH | 0.22 g | 22 hr. |

EXAMPLE 6

This example illustrates the following reduction:

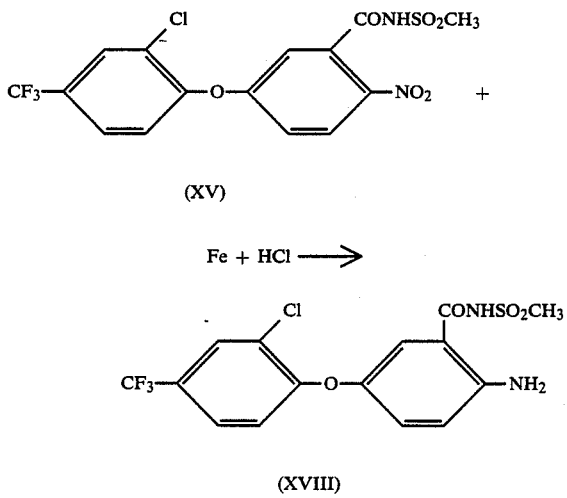

A mixture of 38.2 g (0.087 mole) of (XV), 250 ml of 95% ethanol, and 30 ml (0.36 mole) of concentrated HCl was stirred and warmed to reflux. To this was added 17 g of iron powder in several small portions over 5 minutes. The reaction mixture was heated at reflux for 3 hours. It was then filtered, and the filtrate was concentrated at reduced pressure. The residue was taken up in 400 ml of ethyl acetate, washed with water, dried, and concentrated. 23.5 g of yellow solid product, shown by HPLC to be 81% pure (XVIII) was obtained. Overall yield was 53%.

EXAMPLE 7

This example illustrates the reduction of compound (XV) with dithionite

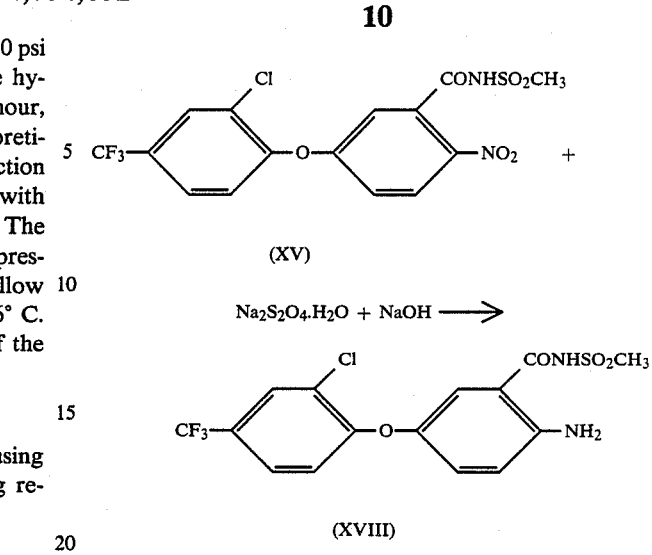

To a solution Of 4.09 g (0.0093 mole) of (XV) in 30 ml of butanol was added dropwise over 30 minutes a solution of 5.7 g (0.030 mole) of sodium dithionite and 2 ml of 6 N NaOH in 30 ml of H$_2$O. An ice bath was used to keep the temperature below 30° C. After addition was complete, the reaction mixture was stirred at ambient temperature for 16 hours. The resulting yellow solution was diluted with 100 ml of toluene and 50 ml of H$_2$O, and the pH was lowered to 1 with concentrated HCl. The water layer was removed, and the organic layer was concentrated to dryness leaving 4.98 g of a yellow solid which was shown by HPLC to be 78% pure (XVIII), giving a quantitative yield of (XVIII).

EXAMPLE 8

This example illustrates the deamination of 2-amino-5-(2-chloro-4-trifluoromethylphenoxy)-N-methanesulfonylbenzamide (XVIII).

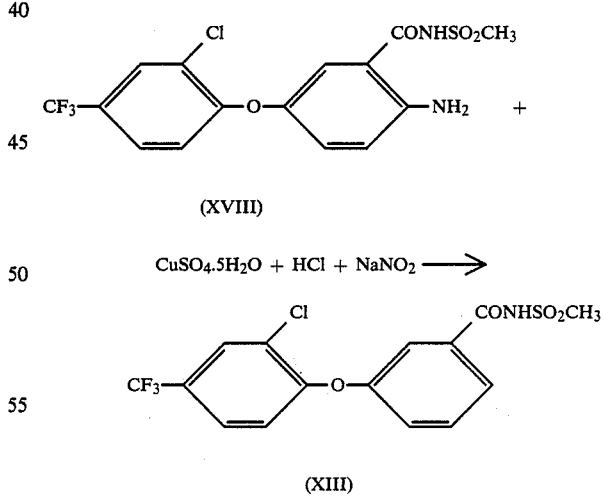

To a stirred slurry of 20.44 g (0.05 mole) of (XVIII) and 0.125 g (0.0005 mole) of CuSO$_4$.5 H$_2$O in 350 ml of ethanol was added 10 ml (0.12 mole) of conc. HCl, followed by dropwise addition of a solution of 3.45 g (0.05 mole) of sodium nitrite dissolved in 22 ml of H$_2$O. The resulting thick slurry was stirred at ambient temperature for 30 minutes, and then was slowly warmed to reflux. Heating at reflux was continued for 30 minutes, after which the reaction mixture was concentrated in vacuo. The yellow residue was partitioned between 500 ml of ethyl acetate and 50 ml of H₂O, and the organic solution was washed with two 50 ml portions of water. The resulting ethyl acetate solution was washed with a saturated NaCl solution, dried, and concentrated. 21.03 g of a yellow solid, mp. 163°–167° C., was obtained. HPLC showed the product to be 82% (XIII), representing an 88% yield.

EXAMPLE 9

This example illustrates the deamination of (XVIII) in Various Solvents with Varying Amounts of Sodium Nitrite.

The procedure of Example 8 was repeated with various solvents and varying amounts of NaNO₂.

| Solvent | eq. NaNO₂ | Yield of (XIII) in Crude Product |
|---|---|---|
| EtOH | 2 | 71% |
| BuOH | 2 | 47% |
| BuOH | 1 | 49% |
| 6:1 BuOH:EtOH | 2 | 52% |
| 19:1 EtOH:BuOH | 2 | 84% |
| 19:1 EtOH:BuOCH₂CH₂OH | 2 | 67% |

EXAMPLE 10

This example illustrates the hydrogenation of a mixtrue of 5-(2-chloro-4-trifluoromethylphenoxy)-N-methanesulfonyl-4-nitrobenzamide, (XVI), and-6-nitrobenzamide, (XVII).

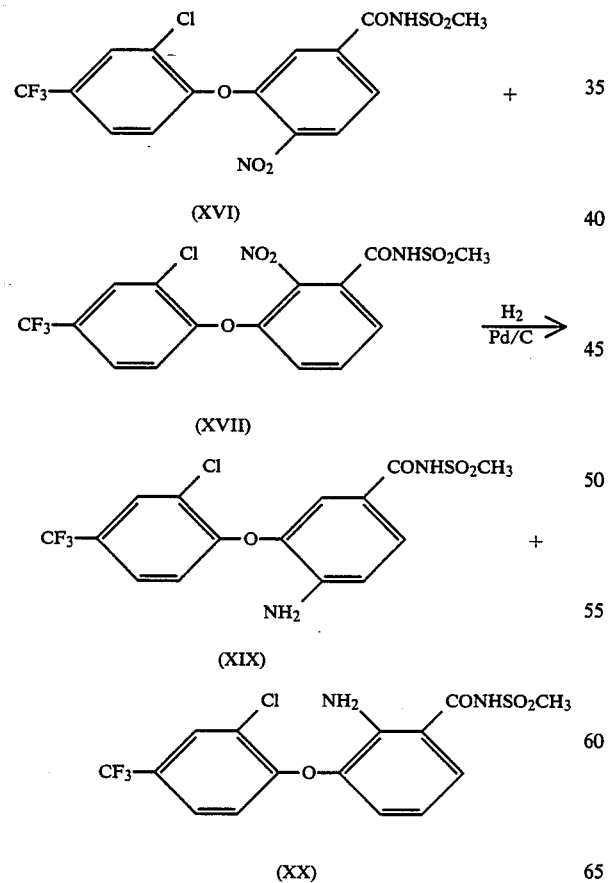

The procedure of Example 2 was repeated except that 11.0 g (0.025 mol) of 5-(2-chloro-4-trifluoromethyl-phenoxy)-N-methanesulfonyl-4-nitrobenzamide and 11.0 g (0.025 mol) of 5-(2-chloro-4-trifluoromethyl-phenoxy)-N-methanesulfonyl-6-nitrobenzamide were substituted for the compound of formula (XV). TLC and IR showed clean conversion to the corresponding amino compounds, represented by formulae (XIX) and (XX). These were separated by prep HPLC (80 CHCl₃: 40 Et₂O: 3 HOAc) to give samples of clean (XIX) and (XX).

EXAMPLE 11

This example illustrates the deamination of a mixture of 4-amino- (XIX), and 6-amino-5-(2-chloro-4-tri-fluoromethylphenoxy)-N-methanesulfonylbenzamide (XX).

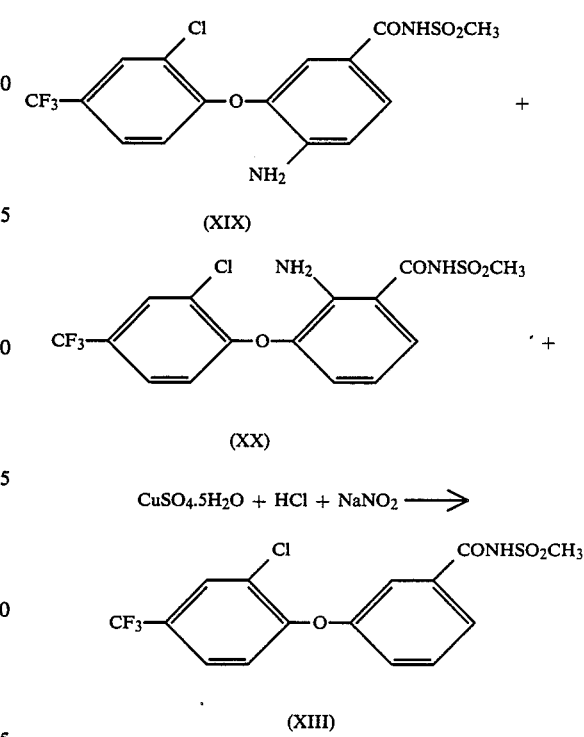

To a stirred mixture of 3.89 g (0.0095 mole) of (XIX), 0.88 g (0.0022 mole) of (XX), 0.03 g (0.00012 mole) of CuSO₄.5 H₂O, and 75 ml of ethanol was added 2 ml (0.024 mole) of concentrated HCl, followed by the dropwise addition of a solution of 0.83 g (0.012 mole) of sodium nitrite in 4 ml of H₂O. The resulting yellow slurry was stirred at ambient temperature for 25 minutes before being slowly warmed to reflux. It was then stirred and heated at reflux for 75 minutes before being concentrated in vacuo. The yellow residue was partitioned between 50 ml of ethyl acetate and 25 ml of water, and the resulting organic solution was washed with two 25 ml portions of water and then with a saturated NaCl solution. After drying, 4.05 g of an orange solid, shown to be 87% pure (XIII) by HPLC, theoretical yield 74% was obtained.

EXAMPLE 12–16

In a Paar Hydrogenator are placed 0.05 mol of Compound A, 100 ml of ethanol and 1.0 g of 5% Pd on carbon (Englehard). The hydrogenator is then pressurized to 60 psi with hydrogen. The mixture is shaken, and the hydrogen is periodically replenished during 1 hour. The reaction mixture is then filtered and the catalyst is then washed with ethyl acetate in order to dissolve the product. The filtrate is then concentrated at reduced pressure.

COMPOUND A

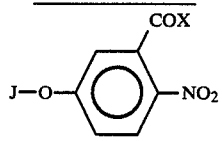

| Example # | J | R$^1$ | R$^2$ | R$^3$ | R$^4$ | R$^5$ | R$^6$ | R$^7$ | B | R$^8$ | X |
|---|---|---|---|---|---|---|---|---|---|---|---|
| 12 | R$^1$-⌬-R$^3$ with R$^2$ | —CF$_3$ | —H | —Cl | —H | — | — | —C$_2$H$_5$ | —OR$^7$ | — | —O—CH(R$^4$)—C(=O)—B |
| 13 | " | —CF$_3$ | —F | —Cl | — | —H | — | | | — | OR$^5$ |
| 14 | " | —CF$_3$ | —H | —Cl | — | —H | — | — | — | — | OR$^5$ |
| 15 | " | —CF$_3$ | —H | —Cl | — | — | —H | — | — | —CH$_3$ | —NR$^6$SO$_2$R$^8$ |
| 16 | " | —CF$_3$ | —H | —Cl | — | — | —H | — | — | —C$_2$H$_5$ | —NR$^6$SO$_2$R$^8$ |

EXAMPLE 17-20

To a stirred solution of 0.05 mole of the reduced compound of Examples 12, 13, 14 and 16 and 350 ml of ethanol is added 0.12 moles of concentrated HCl. A solution of 0.05 mole of sodium nitrate dissolved in 22 ml of H$_2$O is then added dropwise. The slurry is then stirred at ambient temperature for approximately 30 minutes and then is slowly warmed to reflux. Reflux is continued for 30 minutes, after which the reaction mixture is concentrated in vacuo.

EXAMPLE 21

To a stirred slurry of 0.05 mole of the reduced compound of Examples 15 and 16 and 0.0005 mole of CuSO$_4$. 5 H$_2$O in 350 ml of ethanol is added 0.12 mole of concentrated HCl. A solution of 0.05 mole of sodium nitrite dissolved in 22 ml of H$_2$O is slowly added dropwise. The resulting slurry is then stirred at ambient temperature for approximately 30 minutes and is then slowly warmed to reflux. Heating at reflux is continued for approximately 30 minutes, after which the reaction mixture is concentrated in vacuo. The residue is partitioned between 500 ml of ethyl acetate and 50 ml of H$_2$O, and the organic solution is then washed with two 250 ml portions of H$_2$O. The resulting ethyl acetate solution is then washed with a saturated NaCl solution, dried and concentrated.

What is claimed is:

1. A process of recovering and recycling nitrated by-products formed during the manufacture of the compound of the formula

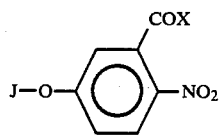

and salts thereof wherein J is

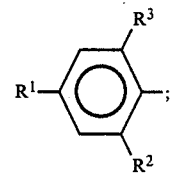

and further wherein:
R$^1$ is fluorine, chlorine, bromine, or iodine or a trifluoromethyl group;
R$^2$ is a hydrogen atom, a fluorine, chlorine, bromine or iodine atom or a trifluoromethyl group;
R$^3$ is a hydrogen atom, a C$_1$-C$_4$ alkyl group, a trifluoromethyl group, a cyano group or a fluorine, chlorine, bromine or iodine group;
X is

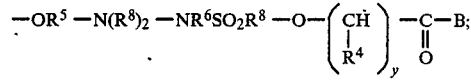

R$^4$ is R$^5$ or an acyl radical of the formula

wherein Alk is a C$_{1-6}$ alkyl group;
R$^5$ is a hydrogen atom or a C$_{1-6}$ alkyl group otionally subsituted with either one or more halogen atoms or a phenyl group;
B is a C$_{1-10}$ alkyl, OR$^7$ or SR$^7$;
y is 1 to 4;
R$^6$ is a hydrogen atom or a C$_{1-2}$ alkyl group;
R$^7$ is hydrogen, or a C$_{1-8}$ alkyl group, a C$_{3-8}$ cycloalkyl group, an agronomically acceptable cationic salt, or a

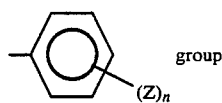 group wherein n is 0 to 3 and Z is selected from the group consisting of halogen, a $C_{1-10}$ alkyl or alkoxy group, cyano, nitro, and trifluoromethyl; and $R^8$ is $R^5$ or a $C_{1-6}$ alkoxy group;

wherein said process comprises:
(a) reducing the nitrated by-products in the presence of either
  (i) Pt or Pd and hydrogen at a pH less than 3
  (ii) an inorganic reducing agent at a pH greater than 8.0, or
  (iii) a strong inorganic acid and a member selected from the group consisting of Fe, Zn Sn, Al, $SnCl_2$, $SnCl_4$, $TiCl_3$, $Ti_3(SO_4)_2$; and
(b) deaminating the reduction product in the presence of sodium nitrite, a mineral acid and a reagent selected from the group consisting of a primary alkanol of 1 to 6 atoms, an alkanolether of the formula $R^9$—O—$R^{10}$—OH wherein $R^9$ and $R^{10}$ are $C_{1-6}$ alkyl and $C_{1-6}$ alkylene groups, respectively, hypophosphorous acid, $CH_2O/OH^-$, a heavy metal, sodium stannite, hydroquinone, ferrous hydroxide, glucose, copper hydride, sodium hydrosulfite and mixture thereof;
(c) isolating the deaminated product of step (b);
(d) nitrating the isolated product of step (c); and (e) repeating steps (a) (b) (c) and (d) until optimum recovery of the compound of formula (I) is obtained.

2. The process of claim 1 which further comprises, recrystallizing the resulting deaminated product of step (c) with a solvent selected from the group consisting of toluene, xylene, chloroform and cyclohexanone.

3. The process of claim 1, wherein said compound of formula (I) has X equal to —$N(R^8)_2$ wherein at least one of $R^8$ is hydrogen; or $NR^6SO_2R^8$ wherein $R^6$ is hydrogen and further wherein the reduction product is deaminated in the presence of $CuSO_4$.

4. The process of claim 1 wherein for the compound of formula (I), X is —$OR^5$ or —$NR^6 SO_2R^8$, $R^5$ and $R^6$ are hydrogen and $R^8$ is methyl or ethyl.

5. The process of claim 3 wherein for the compound of formula (I), $R^1$ is chlorine or trifluoromethyl, $R^2$ is hydrogen or fluorine, and $R^3$ is chlorine.

6. The process of claim 5 wherein $R^1$ is trifluoromethyl, $R^2$ is hydrogen or fluorine, X is —$NR^6SO_2R^8$, $R^6$ is hydrogen and $R^8$ is methyl.

7. The process of claim 5 wherein $R^1$ is trifluoromethyl, $R^2$ is hydrogen, X is —$NR^6SO_2R^8$, $R^6$ is hydrogen and $R^8$ is ethyl.

8. The process of claim 1 wherein for the compound of formula (I), y is 1, X is )

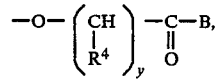

B is $OR^7$, $R^4$ is hydrogen or methyl and $R^7$ is —$C_2H_5$.

9. The process of claim 6 wherein $R^1$ is trifluoromethyl, $R^2$ is fluorine and $R^3$ is chlorine.

10. The process of claim 5 wherein $R^1$ is trifluoromethyl, $R^2$ is fluorine, X is $OR^5$ and $R^5$ is hydrogen.

11. The process of claim 6 wherein $R^1$ is trifluoromethyl, $R^2$ is fluorine and $R^3$ is chlorine.

12. A process of recovering nitrated byproducts formed during the manufacture of the compound of the formula

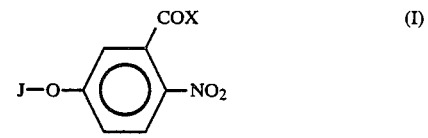 (I)

and salts thereof
wherein J is

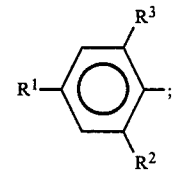;

and further wherein:
$R^1$ is fluorine, chlorine, bromine, or iodine or a trifluoromethyl group;
$R^2$ is a hydrogen atom, a fluorine, chlorine, bromine or iodine atom or a trifluoromethyl group;
$R^3$ is a hydrogen atom, a $C_1$-$C_4$ alkyl group, a trifluoromethyl group, a cyano group or a fluorine, chlorine, bromine or iodine group;
X is either
  (i) —$NR^8$, wherein $R^8$ is hydrogen, a $C_{1-6}$ alkyl group optionally substituted with either one or more halogen atoms or a phenyl group; provided that at least one $R^8$ is hydrogen; or
  (ii) $NR^6SO_2R^8$ wherein $R^6$ is hydrogen and $R^8$ is a hydrogen atom, a $C_{1-6}$ alkyl group optionally substituted with either one or more halogen atoms or a phenyl group wherein said process comprises:
(a) reducing the nitrated by-products in the presence of either
  (i) Pt or Pd and hydrogen at a pH less than 3
  (ii) an inorganic reducing agent at a pH greater than 8.0, or
  (iii) a strong inorganic acid and a member selected from the group consisting of Fe, Zn, Sn, Al, $SnCl_2$, $SnCl_4$, $TiCl_3$, $Ti_3(SO_4)_2$; and
(b) deaminating the reduction product in the presence of (i) sodium nitrite, (ii) a mineral acid, (iii) $CUSO_4$ and (iv) a reagent selected from the group consisting of a primary alkanol of 1 to 6 carbon atoms, an alkanolether of the formula $R^9$—O—$R^{10}$—OH wherein $R^9$ and $R^{10}$ are $C_{1-6}$ alkyl and $C_{1-6}$ alkylene groups, respectively, hypophosphorous acid, $CH_2O/OH^-$, a heavy metal, sodium stannite, hydroquinone, ferrous hydroxide, glucose, copper hydride, sodium hydrosulfite and mixtures thereof; and
(c) isolating the deaminated product of step (b).

13. The process of claim 12 which further comprises nitrating the islated product of step (c) and then repeating steps (a) through (c).

14. The process of claim 13 which further comprises repeating the nitration of isolated product and steps (a) (b) and (c) until optimum recovery of the compound of formula (I) is obtained.

15. The process of claim 12 which further comprises, recrystallizing the resulting deaminated product of step (c) with a solvent selected from the group consisting of toluene, xylene, chloroform and cyclohexanone.

16. The process of claim 12 wherein in step (b) said primary alkanol is ethanol.

17. The process of claim 12 wherein for the compound of formula (I), X is —$OR^5$ or —$NR^6SO_2R^8$, $R^5$ and $R^6$ are hydrogen and $R^8$ is methyl or ethyl.

18. The process of claim 12 wherein for the compound of formula (I), $R^1$ is chlorine or trifluoromethyl, $R^2$ is hydrogen or fluorine, and $R^3$ is chlorine.

* * * * *

UNITED STATES PATENT AND TRADEMARK OFFICE
CERTIFICATE OF CORRECTION

PATENT NO. : 4,754,052
DATED : June 28, 1988
INVENTOR(S) : William W. Brand et al It is certified that error appears in the above-identified patent and that said Letters Patent is hereby corrected as shown below:

In the Specification:

Column 2, line 54, delete the letter "a".

Column 2, line 60, "wherein" should read --wherein X is--.

Column 8, line 46, "-methanessulfo-" should read -- -methanesulfo- --.

In the Claims:

Column 15, line 24, "1 to 6 atoms," should read --1 to 6 carbon atoms,--.

Column 15, line 59, "X is )" should read --X is--.

Signed and Sealed this

Seventh Day of November, 1989

Attest:

JEFFREY M. SAMUELS

Attesting Officer    Acting Commissioner of Patents and Trademarks